US006627394B2

(12) United States Patent
Kritzman et al.

(10) Patent No.: US 6,627,394 B2
(45) Date of Patent: Sep. 30, 2003

(54) DIAGNOSTIC PAD

(75) Inventors: Amnon Kritzman, Zichron Yaakov (IL); Nitsa Galili Nachshon, Kibbutz Geva (IL); Yael Behar, Moshav Ein Ayala (IL)

(73) Assignee: Common Sense Ltd., Caesarea (IL)

( * ) Notice: Subject to any disclaimer, the term of this patent is extended or adjusted under 35 U.S.C. 154(b) by 0 days.

(21) Appl. No.: 09/907,926

(22) Filed: Jul. 19, 2001

(65) Prior Publication Data

US 2003/0017605 A1 Jan. 23, 2003

(51) Int. Cl.[7] .................................................. C12Q 1/00
(52) U.S. Cl. ............................................. 435/4; 435/12
(58) Field of Search ...................... 435/4, 12; 604/358, 604/386

(56) References Cited

U.S. PATENT DOCUMENTS

| 2,664,879 | A |   | 1/1954  | Hardy ............................ 128/2 |
|-----------|---|---|---------|----------------------------------------|
| 3,509,872 | A |   | 5/1970  | Truhan .......................... 128/2 |
| 4,029,597 | A |   | 6/1977  | Neisius et al. ............... 252/408 |
| 4,029,598 | A |   | 6/1977  | Neisuius et al. ............ 252/408 |
| 5,063,930 | A |   | 11/1991 | Nucci ........................ 128/632 |
| 5,094,955 | A |   | 3/1992  | Calandra et al. ........... 435/291 |
| 5,217,444 | A |   | 6/1993  | Schoenfeld ................. 604/361 |
| 5,275,591 | A |   | 1/1994  | Mavinkurve ................ 604/389 |
| 5,304,648 | A |   | 4/1994  | Chen .......................... 544/410 |
| 5,384,411 | A |   | 1/1995  | Robotti et al. ................ 549/31 |
| 5,425,377 | A |   | 6/1995  | Caillouette .................. 128/759 |
| 5,445,147 | A |   | 8/1995  | Schoendorfer et al. ..... 128/632 |
| 5,468,236 | A | * | 11/1995 | Everhart et al. ............ 604/361 |
| 5,823,953 | A |   | 10/1998 | Roskin et al. ............... 600/367 |
| 5,853,669 | A |   | 12/1998 | Wolfbeis .................. 422/82.05 |
| 5,853,699 | A |   | 12/1998 | Maier et al. ............... 424/9.363 |
| 5,876,389 | A |   | 3/1999  | Bouchard et al. ........ 604/385.1 |
| 5,897,834 | A | * | 4/1999  | Lawrence et al. ............ 422/56 |
| 5,925,318 | A |   | 7/1999  | Kruzel et al. ................. 422/56 |
| 6,106,461 | A |   | 8/2000  | Roskin et al. ............... 600/309 |
| 6,126,597 | A |   | 10/2000 | Smith et al. ................. 600/362 |
| 6,149,590 | A |   | 11/2000 | Smith et al. ................. 600/367 |

FOREIGN PATENT DOCUMENTS

GB         2353357 A  *  2/2001  .......... G01N/33/52

OTHER PUBLICATIONS

Mish, F.C. Ed., Merriam–Webster's Collegiate Dictionary, 1993, Merriam–Webster, Inc., Tenth Edition, p. 1139.*
U.S. patent application Ser. No. 09/372,571, Bonstein et al., filed Aug. 1999.

* cited by examiner

*Primary Examiner*—Ralph Gitomer
(74) *Attorney, Agent, or Firm*—Winston & Strawn LLP

(57) ABSTRACT

An indicator system including two pH sensitive indicators and a reagent is disclosed. The indicator system can be integrated into a number of products such as sanitary napkins or panty shields and thus can indicate the presence of amniotic fluid or secretions associated with vaginosis without giving a false positive result upon exposure to urine.

13 Claims, 5 Drawing Sheets

DIAGNOSTIC PAD

FIELD AND BACKGROUND OF THE INVENTION

The present invention relates to the field of medical diagnostics and, more specifically, to an improved substrate and indicator system that are useful, for example, for the diagnosis of medical conditions by identification of vaginal secretions.

Many bodily fluids can be readily identified by chemical properties such as pH One exceptionally useful method of determining the pH of a liquid sample is through the use of an indicator, a chemical compound or combination of compounds, that has a pH dependent color. Well known examples include tea and wine. General details and descriptions of some indicators can be found, for example, in "Indicators", E. Bishop, Pergamon Press, 1972, chapter 3, which is incorporated by reference for all purposes as if fully set forth herein.

Often an indicator is attached to a solid substrate such as paper A sample of a liquid of which the pH needs to be determined is applied to the substrate. The pH of the liquid is determined by determining the color of the indicator present on the substrate. Depending on how the indicator is attached to the substrate, application of the liquid sample may cause the indicator to leach out of the substrate. Since in many applications indicator leaching is undesirable, the indicator is often substantially immobilized on the substrate. One use wherein pH sensitive indicators are immobilized on a substrate is in medical diagnostics, specifically when the indicator is incorporated in a swab, gauze, panty shields, hygienic napkin or related product.

Many medical indications can be diagnosed by identifying the nature of a vaginal secretion. One simple method of identifying a vaginal secretion is using pH. A number of devices involving panty shields and related products configured to allow the identification of vaginal secretions by the use of pH indicators have been disclosed. The user wears the device and whenever there is a secretion it is immediately detected and analyzed by the device.

The use of a sanitary napkin configured to identify the pH value associated with vaginosis or bacterial infections has been described in the art, for example in U.S. Pat. Nos. 5,217,444, 5,823,953 and 6,106,461.

U.S. patent application Ser. No. 09/372,571, incorporated by reference for all purposes as if fully set forth herein, discloses an indicator bound to a hydrophilic synthetic membrane substrate. Further U.S. patent application Ser. No. 09/372,571 discloses a device, such as a panty shield with an indicator bound to hydrophilic synthetic membrane substrate inside of an absorbent material.

A general problem of pH indicators in the diagnosis of medical conditions is that of "false positives". Often a secretion gathered from a bodily location can not be identified with absolute certainly by an indicator due to the existence of a plurality of fluids with a similar pH that may be secreted from that bodily location. Thus existing devices are useful, but do not provide a complete solution for identifying a secretion.

A first example illustrating the difficulty in confident identification is the diagnosis of vaginosis. Vaginal secretions of a patient with vaginosis have a pH between 4.7 and 7.0. Since urine of a healthy patient has a pH between 5.0 and 7.0, it is very difficult to diagnose a secretion as arising from vaginosis with a high degree of confidence by just using a pH based indicator test. One solution known, in the art is to sample fluid from within the vagina, where urine is not ordinarily found. This is discomforting and requires a visit to a health-care professional.

A second example is the identification of amniotic fluid leaking from the vagina of a pregnant woman. During pregnancy amniotic sack integrity may be compromised and a small amount of amniotic fluid may leak out through the cervix and from the vagina. If diagnosed as such, measures such as patient rest or sealing of the amniotic sack using biological glue may be prescribed. If not diagnosed the amniotic sack may later rupture causing abortion of the pregnancy, or require hospitalization of the woman and infant. If the infant is born prematurely, death or severe handicap may be a result. Extended hospitalization of the infant in an incubator is often necessary.

Due to the severe consequences of amniotic fluid leakage, pregnant women undergo severe stress and often go to a health-care professional upon secretion of any liquid from the vicinity of the vagina. The health-care professional looks for the presence of amniotic fluid by checking the pH of the vaginal secretions, amniotic fluid having a pH of between 7.0 and 7.5. Since pregnant women often have urinary incontinence and since urine typically has a pH of between 5.0 and 7.0, if only pH is checked, a false positive result may occur, urine being identified as amniotic fluid. Consequently, it is necessary that such a vaginal secretion be examined using a microscope for the presence of a fern-shaped pattern indicative of amniotic fluid.

As the time between the fluid secretion and the arrival at the health-care professional may be long, there is often no evidence of amniotic fluid upon examination. The secretion is mistakenly assumed to be urine, often with tragic consequences. On the other hand, the health-care professional may decide to err on the side of caution, misdiagnosing the secretion of urine as amniotic fluid leading to an unnecessary hospitalization and concomitant patient stress.

In order to increase the confidence in such diagnoses, a number of systems have been disclosed.

In U.S. Pat. No. 6,149,590 a device in the form of a sanitary napkin with a pH indicator configured to identify the presence of amniotic fluid in a vaginal secretion is disclosed. The device further includes a microscope visualizable slide configured to gather a portion of a vaginal secretion. If the indicator shows the pH corresponding to that of amniotic fluid, the user presents a health-care professional with the slide. The health-care professional examines the slide with the help of a microscope for the typical fern-shaped patterns indicative of the presence of amniotic fluid. A disadvantage of this device is that it requires that the patient visit the health-care professional as a result of any secretion of liquid from the vaginal area.

U.S. Pat. No. 5,897,834, incorporated by reference for all purposes as if fully set forth herein, discloses a device useful in a clinical setting for the confident differentiation between urine and vaginal secretions associated with vaginosis or urine and amniotic fluid. The device includes the use of indicators with a negatively charged group immobilized to a solid polymer substrate containing quaternary ammonium groups. Further the device includes a gaseous amine-releasing reagent and an amine indicator. The use of the polymer substrate containing quaternary ammonium groups is disclosed to have an advantage of sharpening the pH dependent color transition. However, these polymer substrates have been found to be less useful in non-clinical settings: the indicated pH of dried out vaginal secretions is low enough to be misdiagnosed as indicating vaginosis. Thus although the device disclosed in U.S. Pat. No. 5,897,834 is useful in a clinical setting where the health care professional applies the vaginal secretion to the device and observes the color change, if integrated in a patient useable device, such as a panty shield, the device gives abundant false positive results.

There is a need for an indicator system that can differentiate between urine and either amniotic fluid or vaginal secretions related to vaginosis. Further, such a system is ideally useable by the patient to lead to greater peace of mind and to minimize unnecessary hospital visits and the accompanying stress, with few false positive results. The characteristics of such an indicator system must not change due to long use or as a result of a wetting/drying cycle.

SUMMARY OF THE INVENTION

The above and other objectives are achieved by the use of an indicator system and integration into products of the indicator system of the present invention.

According to the teachings of the present invention there is a device with a substrate to which are attached a first pH indicator in an area or areas (hereinfurther termed "first areas"), a second pH indicator in an area or areas (hereinfurther termed "second areas"), and a reagent attached to the substrate in the second areas, where substantial color transitions of each of the two indicators occur at a substantially dissimilar pH. A liquid contacting the substrate interacts with the indicators and the reagent. If the liquid has the pH of a fluid that is to be identified, at least part of the first areas undergoes a substantial color change. The liquid may be an interfering fluid with a pH that changes the color of the first indicator. Therefore, the reagent is selected to react with the interfering fluid (for example), changing the pH of the liquid and consequently substantially changing the color of at least part of the second areas. The presence of the second pH indicator acts as a guarantee against false positive results by allowing a colorimetic differentiation of two fluids with a similar pH. According to a feature of the present invention, the first pH indicator changes color at a substantially lower pH than does the second pH indicator. Usually the first areas are distinct from the second areas. The shape of the areas can be anything, including geometrical shapes, icons and words.

According to a feature of the present invention, the device has an absorbent body in contact with the substrate so that fluids absorbed by the absorbent body wet the substrate. According to a further feature of the present invention, fluid absorbed by the absorbent body must first pass through a microporous membrane.

According to a feature of the present invention the first pH indicator and the second pH indicator both have a substantially negatively charged functional group.

There is also provided according to the teachings of the present invention an absorbent body for absorbing vaginal fluids (for example in the shape of a sanitary napkin, a panty shield or a gauze pad) with an absorbent material in contact with a substrate in such a way that the substrate is wet by fluids absorbed by the absorbent material. To the substrate are attached a first pH indicator in a first areas, a second pH indicator in a second areas, and a reagent attached to the substrate in the second areas, where the color transitions of each of the two indicators occur at a substantially dissimilar pH. According to feature of the present invention, the absorbent body includes a means for mounting the absorbent body in such way that it absorbs fluids secreted from the vicinity of the vaginal area of a female.

There is also provided according to the teachings of the present invention a method for providing an indication of the health condition of a person by providing a substrate to which are attached a first pH indicator in a first areas, a second pH indicator in second areas, and a reagent attached to the substrate in the second areas, where the color transitions of each of the two indicators occur at a substantially dissimilar pH. A liquid (such as liquid secreted from the vaginal area) is applied to the substrate and the first and second areas are inspected for a change in color indicative of the health condition of the person. According to a feature of the present invention, the substrate is retained in the vicinity of a vaginal area of the person for an extended period of time such as minutes, hours or even longer.

According to a feature of the present invention, in all cases hereinabove, the reagent is urease.

According to a further feature of the present invention, in all cases hereinabove, the first pH indicator is configured to substantially change color upon contact with amniotic fluid and the second pH indicator is configured to substantially change color upon contact with urine reacting with the reagent.

According to a still further feature of the present invention, in all cases hereinabove, the first pH indicator is configured to substantially change color upon contact with vaginal secretions associated with vaginosis and the second pH indicator is configured to substantially change color upon contact with urine reacting with the reagent.

There is also provided according to the teachings of the present invention a method of attaching an indicator to a substrate. The substrate can be made of many materials including polypropylene membranes, paper or cotton, and can be of many structures including of a membrane, fabric, mesh, gauze, thread, fiber and a sheet. A mixture of preformed polymer (such as a cellulose), a plasticizer, a wetting agent, an ion-balance reagent and an indicator (alone or with a reagent such as urease) is prepared. In some cases it is preferable to add a solvent to the mixture. The mixture is applied to a substrate for example by dipping the substrate in the mixture or by spraying or spreading the mixture onto the substrate. The substrate with the applied mixture is allowed to dry. When dry, the indicator is bound to the substrate with the help of the polymer. This method is exceptionally useful when the indicators have a substantially negatively charged functional group such as an acetate or a sulfonate.

There is also provided according to the teachings of the present invention an additional method of attaching an indicator to a substrate, especially a neutral substrate, by applying a surfactant solution to the substrate and letting it dry (preferably under vacuum). Once the surfactant is dry, an indicator solution (or a solution with a reagent, such as urease) is applied to the substrate and allowed to dry (also preferably under vacuum). When the indicator to be attached to the substrate has a substantially negatively charged functional group, a cationic surfactant is preferably used.

BRIEF DESCRIPTION OF THE DRAWINGS

The invention is herein described, by way of example only, with reference to the accompanying drawings, where.

DETAILED DESCRIPTION OF THE INVENTION

Before turning to details of the present invention, it should be appreciated that the present invention provides a method, an indicator system, a device and a substrate for identification of a sample liquid as a specific fluid when there is a possibility for the presence of an interfering fluid with a similar pH. The present invention is configurable to be used by an untrained person with heretofore-unknown confidence in the results.

The indicator system of the present invention can be implemented using many devices and methods. In a preferred embodiment, the indicator system of the present invention is implemented in a manner that can be easily used by non-skilled personnel, specifically a user. For the two cases specifically mentioned hereinabove, the indicator system of the present invention can be supplied to the user, for example, in the form of a pad, a swab, a fiber ball, but most preferably, as a sanitary napkin or panty shield. Details of manufacture of swabs, fiber-balls, pads, panty shields or sanitary napkins, including the attachment of indicators to substrates, are well known to one skilled and have been fully described in the prior art, for example U.S. Pat. Nos. 5,217,444, 5,897,834, 6,149,590 or in U.S. patent application Ser. No. 09/372,571.

Figure 2:
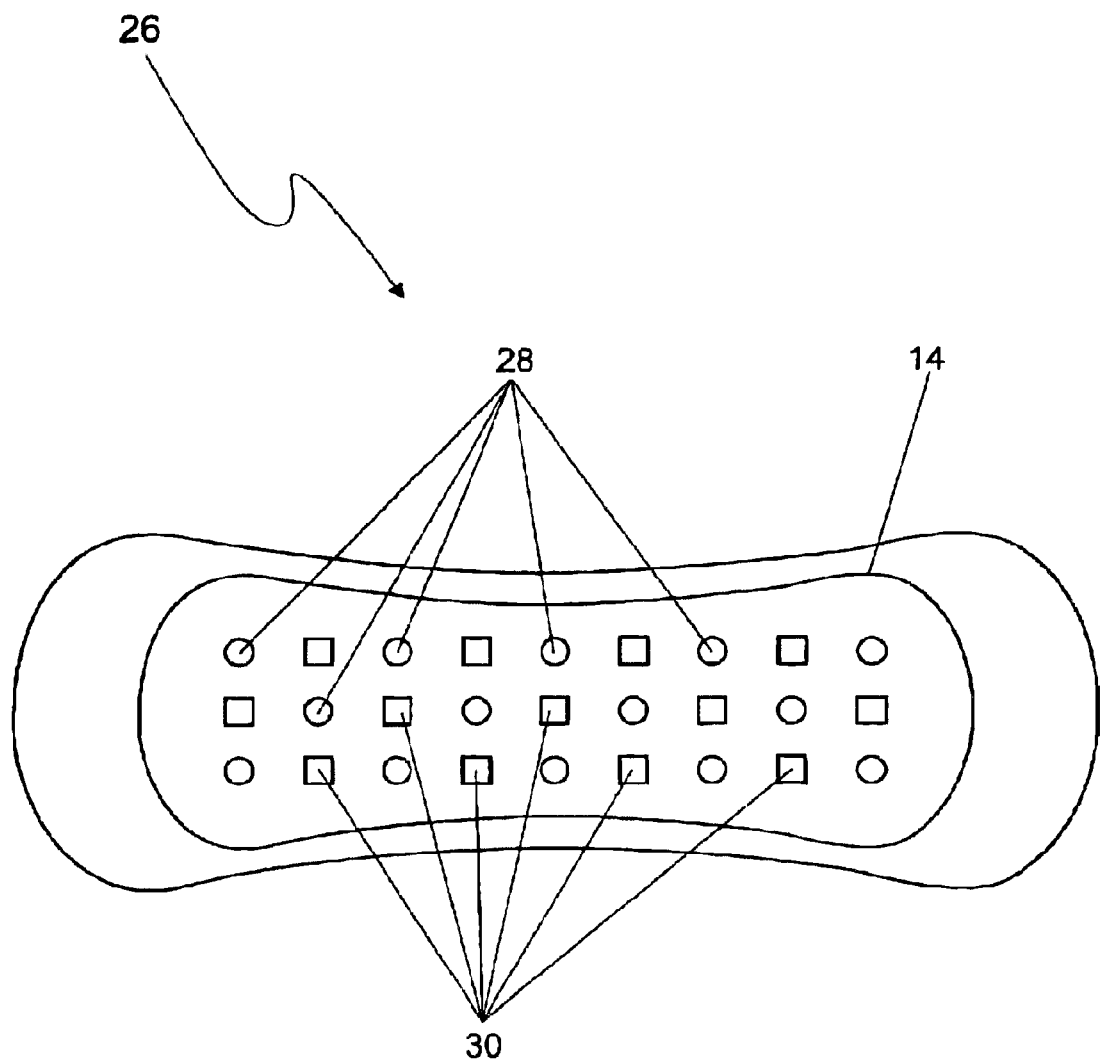
FIG. 2 is a schematic top view of a different embodiment of the device of the present invention.
Figure 3:
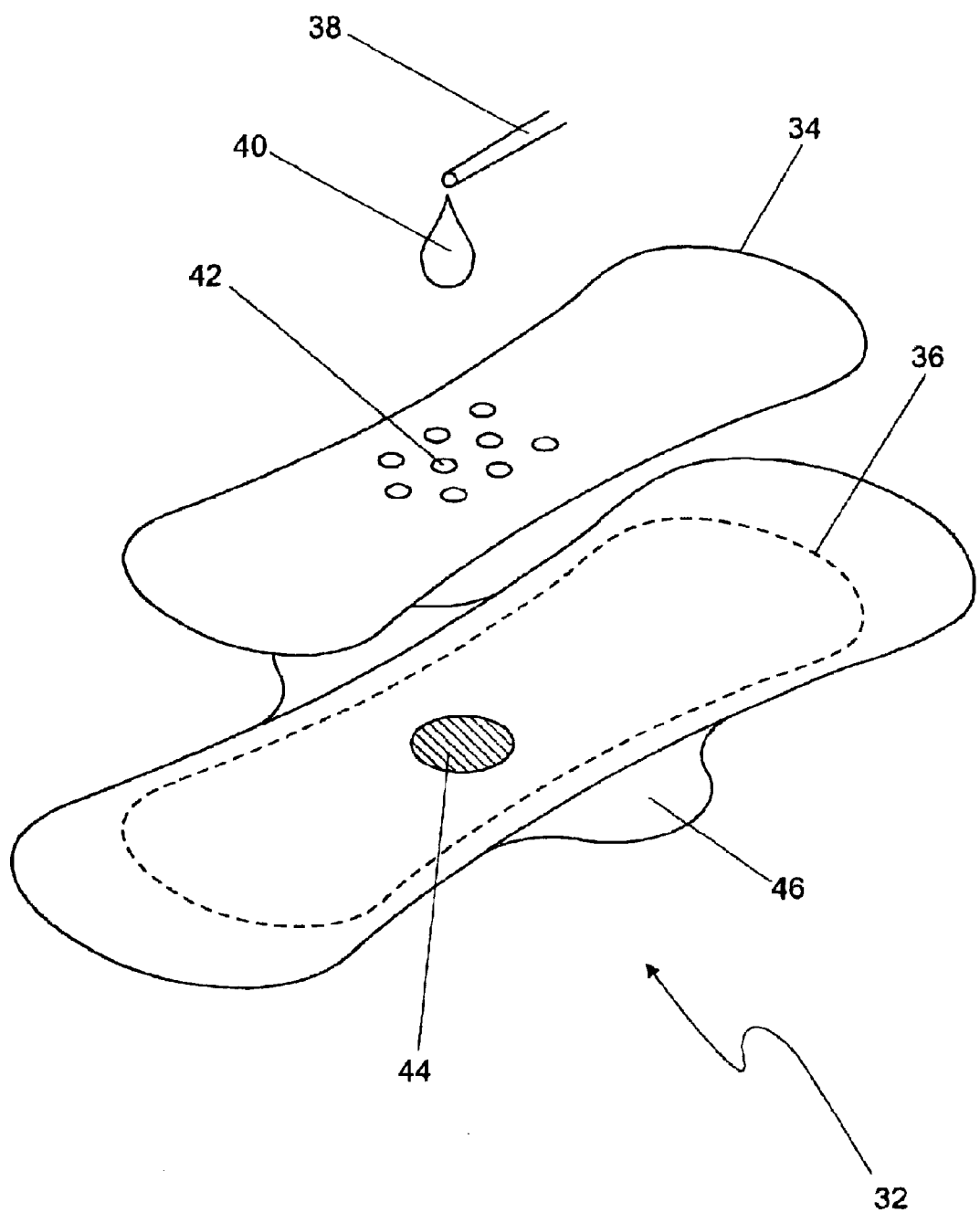
FIG. 3 is a schematic perspective view of a different embodiment of the device of the present invention with a microporous membrane.

The principles of the methods and operation of the present invention are better understood with reference to the figures and the accompanying description. The present invention will be exemplified by embodiments of the device of the present invention in the form of a panty shield in FIGS. 1, 2 and 3 configured to identify either amniotic fluid or vaginal secretions associated with vaginosis where the possibility exists that the presence of urine will cause a false positive response.

Method for Identification of Fluids

As discussed hereinabove, known methods for identifying a fluid using pH sensitive products fail when there exists an interfering fluid with a similar pH. This is exemplified by the similar pH of urine and amniotic fluid or urine and vaginal secretions resulting from vaginosis. Known methods for overcoming these limitations are useful only in clinical settings.

To overcome these problems, the present invention provides an indicator system made up of a first indicator, a second indicator and a reagent as well as a method and a device for implementing the indicator system.

Figure 1A:
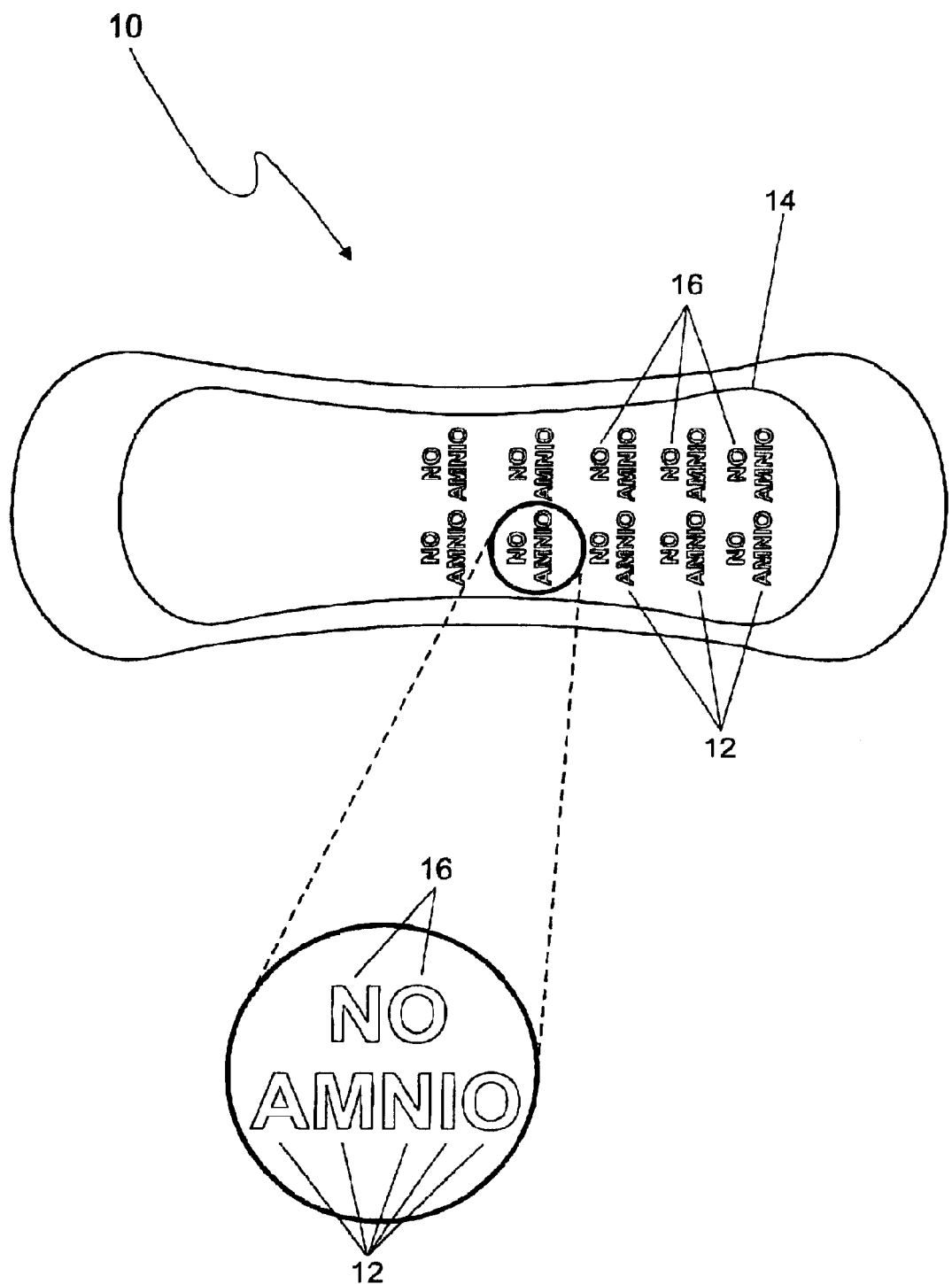
FIGS. 1A–1C are schematic top views of an embodiment of the device of the present invention with magnification of details of indicators applied to the substrate.

The first indicator of the system of the present invention is chosen so as to identify a first pH. The first pH corresponds to the pH of the fluid that is to be identified. Further, the first pH may also be that of an interfering fluid. When amniotic fluid is to be identified, a first indicator is chosen to indicate that a tested vaginal secretion has a pH of amniotic fluid. Due to the similar pH of urine and amniotic fluid, such a first indicator will also change color when exposed to urine. When vaginosis is to be diagnosed, a first indicator is chosen to indicate a pH typical of secretions of vaginosis and consequently also of urine. In FIG. 1A, a first indicator is applied at first areas 12 on a substrate 14 integrated in a panty shield 10. First areas 12 may be arranged as patterns, letters, words or icons, as described in U.S. Pat. No. 5,897,834. In FIG. 1, first indicator is nitrazine yellow, which is yellow at a pH below 7 and blue violet at a pH above 7.

The reagent of the indicator system of the present invention is chosen so as to yield reaction products that substantially change the pH of a tested secretion when the tested secretion is either the fluid to be identified or is the interfering fluid, or both. If the reagent is chosen so as to react with both fluids, it is clear to one skilled in the art that the pH change resulting from reaction with the fluid to be identified is different from the pH change resulting from the reaction with the interfering fluid. In one preferred non-limiting embodiment of the present invention, when either amniotic fluid is to be identified or vaginosis is to be diagnosed, urease (CAS 9002-13-5) is chosen as the reagent. If urine is present, the urine reacts with the urease, releasing ammonia into the tested secretion raising its pH to well above the pH of either amniotic fluid or vaginosis related secretions.

The second indicator of the system of the present invention is chosen so that it indicates the change of pH as a result of the reaction with the reagent. For example, second indicator in FIG. 1 is m-cresol purple, m-cresol purple is yellow at a pH of below 7.5 and is violet at a pH above 8.0. The second indicator and the reagent are applied at second areas 16 on substrate 14, distinct from the first areas 12 on substrate 14, FIG. 1A.

Figure 1B:
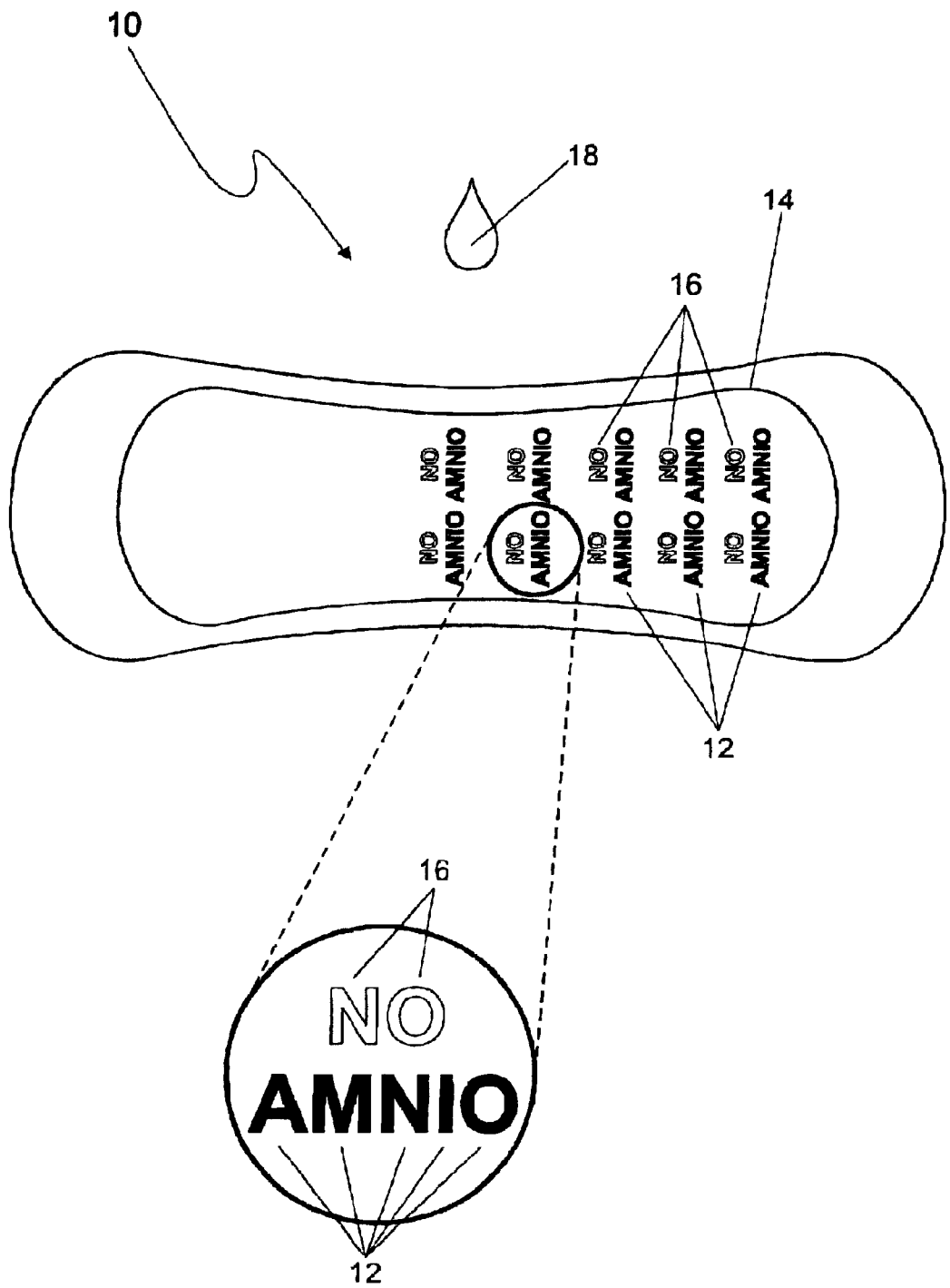

In FIG. 1B, amniotic fluid 18 comes in contact with panty shield 10. Amniotic fluid 18 makes contact with first areas 12, and second areas 16. As the pH of amniotic fluid 18 is between 7.0 and 7.5, the nitrazine yellow present at first areas 12 become blue violet, spelling out the word "AMNIO". It is clear to one skilled in the art that if a small amount of fluid is applied to panty shield 10, it is possible that only part of first areas 12 will change color. The m-cresol purple present at second areas 16 remains yellow.

When the user of panty shield 10 in FIG. 1B examines panty shield 10, she reads the word "AMNIO" and can go to a health-care professional who can take action corresponding to a high degree of certainty of amniotic fluid secretion.

Figure 1C:
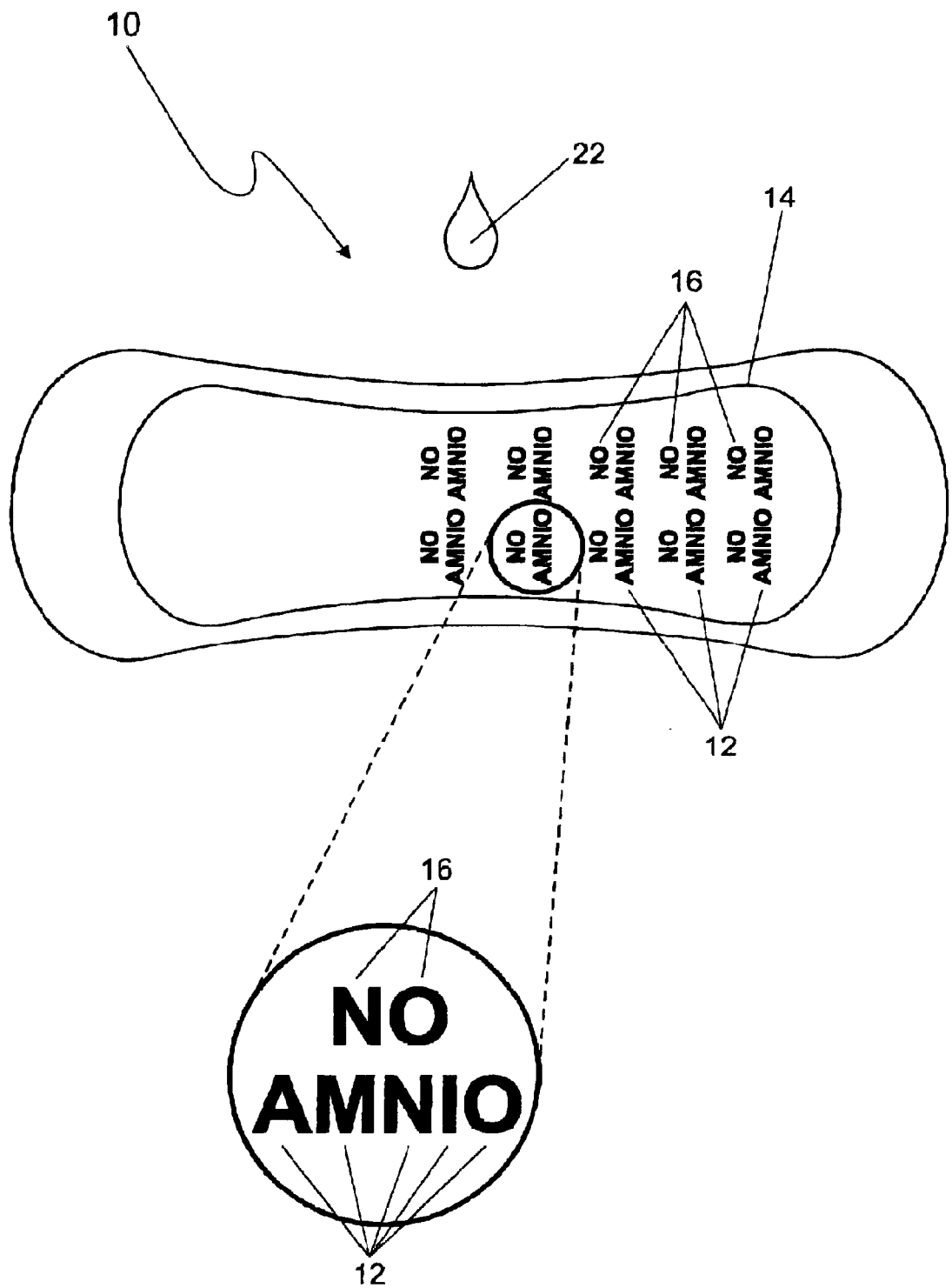

In FIG. 1C, urine 22 comes in contact with panty shield 10. Urine 22 makes contact with first areas 12 and second areas 16. As the pH of urine 22 is 7.2, the nitrazine yellow present at first areas 12 becomes blue violet, spelling out the word "AMNIO". Urine 20 reacts with urease present at second areas 16, releasing ammonia. The ammonia increases the pH of the liquid present in second areas 16 to pH 9. As a result of the high pH, m-cresol purple present at second areas 16 becomes violet, spelling out the word "NO".

TABLE 1

| indicator | aqueous pH transition range | color change | CAS |
| --- | --- | --- | --- |
| 1 Cresol Red | 7.2–8.8 | yellow to reddish purple | 1733-12-6 |
| 2. Alizarin | 5.5–6.8 | yellow to violet | 72-48-0 |
| 3. Bromocresol Purple | 5.2–6.8 | yellow to purple | 115-40-2 |
| 4 Chlorophenol Red | 5.2–8.8 | yellow to red | 4430-20-0 |
| 5 Nitrazine Yellow | 6.0–7.2 | yellow to bright blue | 5423-07-4 |
| 6 Bromothymol Blue | 6.0–7.6 | yellow to blue | 34722-90-2 |
| 7 Bromoxylenol Blue | 6.0–7.6 | yellow to blue | 40070-59-5 |
| 8 Neutral Red | 6.8–8.0 | red to yellow | 553-24-9 |
| 9. Phenol Red | 6.8–8.2 | yellow to red | 34487-61-1 |
| 10 Thymol Blue | 8.0–9.2 | yellow to blue | 81012-93-3 |
| 11 Xylenol Blue | 8.0–9.6 | yellow to blue | 125-31-5 |
| 12. m-Cresol purple | 7.4–9.0 | yellow to purple | 2303-01-7 |

When the user of panty shield 10 panty shield 10 in FIG. 1C examines panty shield 10, she reads the words "NO AMNIO". The user who became agitated at the unexpected loss of fluid is immediately calmed and is relieved of the necessity of a stressful visit to a health-care professional. It is clear to one skilled in the art that arranging first areas 12 and second areas 16 so as to spell out words is not necessary, and in alternative embodiments of the present invention first areas 12 and second areas 16 may have any shape. For example, in FIG. 2, a panty shield 26 configured in accordance with the present invention is depicted where each one of first areas 28 are of substantially circular shape and each one of second areas 30 are substantially square shaped.

When used in a medical setting, it is imperative that there be substantially no leaching of indicator system components from the substrate to which the indicator system is attached. The attachment of indicators to a substrate is well within the ability of one skilled in the art, see for example U.S. patent application Ser. No. 09/372,571. One family of chemical compounds that are suitable for use as a first indicator and a second indicator of the present invention without leaching are indicators with negative functional groups. Suitable indicators include nitrazine yellow, thymol blue, bromothymol blue, xylenol blue, bromoxylenol blue, phenol red, m-cresol purple, chlorophenol red, bromocresol purple, alizarin, neutral red, and cresol red, see Table 1. A list of other suitable indicators can be found, for example, in U.S. Pat. No. 5,897,834. It is clear to one skilled in the art that the indicators specifically mentioned herein are just examples and any suitable indicators may be used. Further, there may be instances where the first indicator and/or the second indicator are made up of a combination of individual indicators, see for example U.S. patent application Ser. No. 09/372,571.

A second non-limiting embodiment of the indicator system of the present invention is a device for the identification of vaginal infections such is bacterial vaginosis (BV). According to the present invention, an indicator system is made with a first indicator that indicates the presence of a fluid with a pH of around 4.7 to 7.0. The first indicator can be chosen, for example, from one or more of the group including nitrazine yellow, bromothymol blue and bromoxylenol blue. As can be seen in Table 1, these three indicators typically exhibit a bluish color when exposed to a fluid with a pH above 7.0. The second indicator can be chosen, for example, from the group including phenol red, thymol blue, xylenol blue and m-cresol purple. As can be seen in Table 1, upon exposure to a fluid with a pH above 8.0 these four indicators become red, blue, violet and violet, respectively. The reagent added to the second embodiment of the device of the present invention is, for example, urease.

As discussed hereinabove, urine of a healthy patient has a pH between 5.0 and 7.0. A patient having BV also has vaginal secretions with a pH between 4.7 and 7.0. If the liquid examined in the second embodiment of the device of the present invention is associated with BV, the first indicator changes color whereas the second indicator remains yellow. If the liquid examined contains urine, the first indicator changes color. Further, the urease reacts with the urine producing ammonia, raising the pH of the fluid, and consequently causing the second indicator to change color.

Improved Methods for Attaching Indicators to a Substrate

Details and variations concerning the method of manufacture of a device for implementing the indicator system of the present invention or applying the method of the present invention are well described in the prior art.

As described hereinabove, U.S. Pat. No. 5,897,834 describes a solid pre-formed polymer to which quaternary ammonium groups are covalently bound. Negatively charged indicators are non-covalently bound to the polymer. The non-covalent bonds are strong enough so that the attached indicators do not leach out in an aqueous solution. In addition, the indicators bound to the polymer have a sharpened pH color transition, allowing an accurate determination of the pH of the applied fluid. The polymer can be applied to various substrates. However, indicators bound to these polymers are less useful in non-clinical settings as the indicated pH of vaginal secretions after drying is lower than that of fresh vaginal secretions, leading to a false positive results.

In the present invention is disclosed a method suitable for attaching indicators to a substrate so that the indicators do not leach out in an aqueous fluid. Especially suitable indicators are those with a negatively charged group, such as those listed in Table 1 or, for example, in U.S. Pat. No. 5,897,834. The polymer of the present invention is exceptionally suited for attaching the indicator system of the present invention to substrate. Further, experiments show that unlike other methods and polymers known in the art, changes in color of indicator attached according to the methods of the present invention are fast. The color is retained over a long period of time and even when the applied liquid dries. Repeated cycles of drying and wetting also do not change the color. Thus, in practical terms, there is time for a user to get to a health care professional without the color of the indicator changing.

Application of Indicator to a Substrate in General

In a first embodiment of a method of attaching an indicator to a substrate according to the present invention, an indicator is mixed with a preformed polymer in a suitable solution and then applied to a substrate.

In more detail, a polymer solution is prepared containing dry pre-formed polymer, plasticizer, a wetting agent, an ion-balance reagent, a solvent and an indicator. When practicing the method of the present invention, a reagent as described is also added.

The preformed polymer can be selected from various preformed polymers, although cellulose polymers such as nitrocellulose, cellulose acetate or ethyl cellulose are preferred. The preformed polymer makes up 20% to 50% of the weight of the solution. Preferred is that the polymer makes up 25% to 45% of the solution, more preferred is that the polymer makes up 30% to 43% of the solution, and most preferred is that the polymer makes up 36% to 39% by weight of the solution. As is clear to one skilled in the art, it is also possible to use a combination of suitable preformed polymers when making one polymer solution.

Although any suitable plasticizer can be used, bis-(2-butoxyethyl) adipate (BBPA, CAS 141-18-4), bis-(2-ethylhexyl) sebacate (DOS, CAS 122-62-3), diethyl phthalate (DEP, CAS 84-66-2) or dibutyl phthalate (DBP, CAS 84-74-2) are preferred. The plasticizer makes up 15% to 40% of the weight of the solution. Preferred is that the plasticizer makes up 20% to 35% of the solution, more preferred is that the plasticizer makes up 25% to 31% of the solution, and most preferred is that the plasticizer makes up 27% to 29% by weight of the solution. As is clear to one skilled in the art, it is also possible to use a combination of suitable plasticizers when making one polymer solution.

Although any suitable wetting agent can be used, triethylene glycol, ethylene glycol, sorbitol or 2-ethoxy ethanol are preferred. The wetting agent makes up 15% to 45% of the weight of the solution. Preferred is that the wetting agent makes up 21% to 40% of the solution, more, preferred is that the wetting agent makes up 26% to 34% of the solution, and most preferred is that the wetting agent makes up 29% to 31% by weight of the solution. As is clear to one skilled in the art, it is also possible to use a combination of suitable wetting agents when making one polymer solution.

Although any suitable ion-balance reagent can be used, tricaprylylmethyl ammonium chloride (Aliquat 336, CAS 5137-55-3), tridodecylmethyl ammonium chloride (TDMAC, CAS 7173-54-8) or cetyltrimethyl ammonium chloride (CTAC, CAS 112-02-7) are preferred. The ion-balance reagent makes up 0.1% to 10% of the weight of the solution. Preferred is that the ion-balance reagent makes up 1% to 8% of the solution, more preferred is that the ion-balance reagent makes up 3% to 7% of the solution, and most preferred is that the ion-balance reagent makes up 4% to 6% by weight of the solution. As is clear to one skilled in the art, it is also possible to use a combination of suitable ion-balance reagents when making one polymer solution.

The components of the solution are added so that the sum of weights of pre-formed polymer, plasticizer wetting agent and ion-balance reagent is equal to 100%.

The desired indicator is added to the solution. Although any suitable indicator can be used, it is preferred that the indicator molecules have a negatively charged functional group such as acetate or sulfonate. Most preferably, the indicators used, separately or in combination, are chosen from amongst indicators listed in Table 1 and in U.S. Pat. No. 5,897,834. The total amount of indicator added is 0.05% to 5% of the weight of the polymer solution as described above. Preferred is that the indicator is 0.05% to 3% of the polymer solution, more preferred is that the indicator is 0.1% to 1% of the polymer solution, and most preferred is that the indicator is 0.2% to 0.4% of weight of the polymer solution.

When it is desired to add a reagent in preparation of the indicator system of the present invention, reagent is added to the polymer solution. For example, when urease is used, any suitable amount of urease can be added although it is preferred that the concentration of urease is about 10 units for each 0.01%–0.1% of indicator added to the polymer solution.

Further, an amount of solvent is added that is suitable for making any easily applied solution/indicator mixture. Typically, 150 mg of polymer solution is dissolved in between 1 ml and 30 ml of solvent, preferably between 5 ml and 15 ml solvent. Although any suitable solvent or mixture of solvents may be used, preferred are ethyl acetate or substantially volatile ethers such as diethyl ether, isopropyl ether, t-butyl methyl ether or tetrahydrofuran.

Once the mixture is ready, it is applied by suitable means to the substrate. Application can be done, for example, by spraying or spreading the mixture on the substrate, or by dipping the substrate in the mixture. The substrate can be of many suitable materials known in the art such as polyester membranes, polypropylene membranes, cellulose membranes, paper, cotton or linen. The structure of the substrate may be, for example, a fiber, a mesh, gauze, a fabric or a membrane. The solvent of the mixture is allowed to evaporate. Once the mixture dries onto the substrate, the substrate is integrated into whatever device is desired, such as a panty shield.

As is clear to one skilled in the art that when the indicator system of the present invention is implemented, a first mixture with a first indicator is made, and a second mixture with a second indicator and a reagent is made, both mixtures as described hereinabove. Each of the two mixtures is applied to areas on the substrate, as described hereinabove. Preferably the areas of application of The first mixture is substantially distinct from the area of application of the second mixture.

In certain applications, the liquid to be tested may contain biological polymers such as proteins or fats. For example, amniotic fluid and urine often contain proteins. The biological polymers may plug up the pores in the substrate reducing the effectivity of the testing method. This can be exceptionally significant in panty shield applications such as panty shield 32 depicted in FIG. 3. In such a case, it is preferable to interpose a microporous membrane 34, such as a dialysis membrane (e.g., cellulose membrane, catalog nr. D-9402, Sigma-Aldrich, St Louis Mo.), between indicator substrate 36 and a source 38 of secretion 40. Large-sized materials 42 in secretion 40 cannot penetrate microporous membrane 34 whereas fluid component 44 of secretion 40 penetrates microporous membrane 34 to react with indicator substrate 36. Panty shield 32 in FIG. 3 further includes two side flaps 46 (only one is visible in FIG. 3) configured to allow attachment of panty shield 32 to an undergarment of a user, in such a way keeping panty shield 32 in the proximity of the vagina of a user.

Application of Indicator to a Substrate

In a second embodiment of a method of attaching an indicator to a substrate according to the present invention, a substrate is first treated with a surfactant solution. After the solution dries, an indicator solution is applied to the substrate. The substrate can then be integrated into a product.

Although any surfactant can be used, when it is desired to attach negatively charged indicators to a neutral substrate a surfactant with a cationic functional group is used, preferably Aliquat 336, TDMAC or CTAC. Although any suitable solvent or mixture of solvents may be used, preferred are ethyl acetate or substantially volatile ethers such as diethyl ether, isopropyl ether, t-butyl methyl ether or tetrahydrofuran. The surfactant is dissolved in the solvent at any suitable concentration. Preferred is that the surfactant makes up 0.01% to 2% of the solution, more preferred is that the surfactant makes up 0.1% to 0.5% of the solution, and most preferred is that the surfactant makes up 0.15% to 0.25% by weight of the solution. As is clear to one skilled in the art, it is also possible to use a combination of suitable surfactants. The surfactant solution is applied to the substrate. Application is done, for example, by spraying or spreading the mixture on the substrate, or by dipping the substrate in the mixture. The substrate can be of many suitable materials known in the art such as polyester membranes, polypropylene membranes, cellulose membranes, paper, cotton or linen. The structure of the substrate may be, for example, a fiber, a mesh, gauze, a fabric or a membrane. The solvent of the surfactant solution is allowed to evaporate. Although the solvent may be allowed to evaporate at ambient pressure, it is preferable to evaporate the solvent under vacuum, preferably at a pressure of less than 600 mm Hg, more preferably less than 200 mm Hg, and even more preferably less than 100 mm Hg.

After the solvent of the surfactant solution has evaporated, an indicator solution is applied to the substrate. Although any solvent or mixture of solvents may be used, preferred are ethyl acetate or substantially volatile ethers such as diethyl ether, isopropyl ether, t-butyl methyl ether, or tetrahydrofuran. Although any suitable indicator can be used, it is preferred that the indicator molecules have a negatively charged functional group such as acetate or sulfonate when the surfactant used is a cationic surfactant Most preferably, the indicators used, separately or in combination are chosen from amongst those listed in Table 1 or, for example, in U.S. Pat. No. 5,897,834. The amount of indicator added is 0.00001% to 1% of the weight of the indicator solution as described above. Preferred is that the indicator is 0.0001% to 0.1% of the indicator solution, more preferred is that the indicator is 0.001% to 0.01% of the indicator solution, and most preferred is that the indicator is 0.002% to 0.004% of weight of the indicator solution.

When it is desired to add a reagent in preparation of the indicator system of the present invention, reagent is added to the indicator solution. For example, when urease is used, any suitable amount of urease can be added. Although any suitable concentration of urease can be used, preferred is a concentration of between 1 and 100 unit/ml, more preferred is a concentration of 2 and 50 unit/ml and even more preferred a concentration of 5 and 20 unit/ml.

In an additional embodiment of the present invention, a reagent solution is prepared separately from the indicator solution. When urease is used as a reagent, any suitable concentration of urease can be used. It is preferred that a concentration of between 1 and 100 unit/ml urease be used, more preferred is a concentration of 2 and 50 unit/ml and even more preferred a concentration of 5 and 20 unit/ml.

The indicator solution (or indicator/reagent solution) is applied to the substrate. Application can be done, for example, by spraying or spreading the indicator solution on the substrate, or by dipping the substrate in the indicator solution. The solvent of the indicator solution is allowed to evaporate. Although the solvent may be allowed to evaporate at ambient pressure, it is preferable to evaporate the solvent under vacuum, preferably at a pressure of less than 600 mm Hg, more preferably less than 200 mm Hg, and even more preferably less than 100 mm Hg.

When a reagent solution is prepared separately from the indicator solution, the reagent solution is applied in substantially the same way as described hereinabove, either before or after application of the indicator solution.

Irrespective of the exact concentration of the indicator solution and of the surfactant solution used, it is preferable to apply an amount of each one of the solutions so that the molar concentration of surfactant applied per unit area of substrate is roughly one hundred times greater than the molar concentration of indicator applied per unit area of substrate. The indicator solution is applied to the substrate to areas where surfactant was previously applied.

As is clear to one skilled in the art, when the indicator system of the present invention is implemented, a first solution with a first indicator is made, and a second solution with a second indicator and a reagent is made, both solutions as described hereinabove. Each of the two solutions is applied in distinct areas on the substrate, as described hereinabove.

EXAMPLE 1

Solution A: 370 mg cellulose acetate, 280 mg DBP, 150 mg sorbitol, 150 mg 2-ethoxyethanol, 50 mg TDMAC wee combined. 3 mg bromothymol blue were added. 20 ml THF were added. The solution was vigorously stirred.

Solution B: 370 mg cellulose acetate, 280 mg BBPA, 300 mg ethylene glycol, 50 mg TDMAC were combined 3 mg m-cresol purple and 30 units urease were added. 20 ml THF were added. The solution was vigorously stirred.

1a. Cotton gauze was dipped in Solution A. When the solution dried, the cotton gauze was cut in half. The first half was dipped in a pH7 test solution. The first half became purple. The first half was allowed to dry in ambient conditions, with no substantial change of color. After three hours, the second half was dipped in a pH 7 test solution. The second half became purple. The colors of the first half and of the second half were substantially the same.

1b. Cotton gauze was dipped in Solution B When the solution dried, the cotton gauze was cut in half. The first half was dipped in urine. The first half became violet. The first half was allowed to dry in ambient conditions, with not substantial change of color. After the hours, the second half was dipped in urine. The second half became violet. The colors of the first half and of the second half were substantially the same.

1c. Solution A and Solution B were applied in alternating stripes on cotton gauze at a density of about 50 ul/mm$^2$. Amniotic fluid was applied to the gauze, changing the color of the stripes of Solution A to purple. Urine was applied to the gauze, changing the color of the stripes of Solution B to violet. The gauze was allowed to dry at ambient conditions for three hours and cut in half. Urine was applied to the first half. The colors of the stripes in the first half and the second half of the gauze were substantially the same.

EXAMPLE 2

Three solutions were prepared.

Solution A: 0.2% Aliquat 336 in DDW (double distilled water);

Solution B: 10 unit/ml urease and 0.003% m-cresol purple in DDW; and

Solution C: 0.003% nitrazine yellow in isopropyl ether.

A nitrocellulose membrane was dipped in Solution A and transferred to an atmosphere of 50 mm Hg. After 30 minutes, the membrane was removed from the vacuum. Solution B was applied in a pattern resembling the word "NO" at a density of 50 ul/mm$^2$. Solution C was applied in a pattern resembling the word "AMNIO" at a density of 50 ul/mm$^2$. The membrane was transferred to an atmosphere of 50 mm Hg. After 30 minutes, the membrane was removed from the vacuum. The membrane was dipped in a pH 7 test solution. The word AMNIO appeared in purple. After drying at ambient conditions for three hours, no substantial change of color was observed. The membrane was dipped in urine. The word NO appeared in violet.

It is clear to one skilled in the art that the present invention is not limited to the embodiments described herein but also relates to all kinds of modifications thereof, insofar as they are within the scope of the claims.

What is claimed is:

1. A diagnostic device for detection of vaginosis or amniotic fluid leakage without giving a false positive result due to contact with urine, the device comprising:

a substrate, and an indicator system being attached to the substrate, the indicator system including:

a first indicator attached to the substrate in one or more first areas;

a second indicator attached to the substrate in one or more second areas; and a reagent comprising urease attached to the substrate in the one or more second areas.

wherein the first indicator is configured to change color when contacted by a vaginal secretion having a pH level associated with vaginosis or amniotic fluid leakage and the second indicator is configured to change color when contacted by urine reacting with the reagent, while not changing color when contacted by vaginal secretions having a pH level associated with vaginosis or amniotic fluid leakage.

2. The device of claim 1, wherein the substrate, first pH indicator and the second indicator are configured so that a color attained upon a color transition remains unchanged three hours after drying.

3. The device of claim 1, further comprising an absorbent body in contact with the substrate so that the substrate is wet by fluids absorbed by the absorbent body.

4. The device of claim 3, wherein fluids absorbed by the absorbent body passes through a microporous membrane prior to absorption by the absorbent body.

5. The device of claim 1, wherein the first indicator is configured to change color upon contact with amniotic fluid.

6. The device of claim 1, wherein the first indicator is configured to change color upon contact with vaginal secretions associated with vaginosis.

7. The device of claim 1, wherein the first indicator and the second indicator each have a negatively charged functional group.

8. An absorbent diagnostic device for detection of vaginosis or amniotic fluid leakage without giving a false positive result due to contact with urine, the device comprising:
   an absorbent body;
   a substrate in contact with the absorbent body, and
   an indicator system being attached to the substrate, the indicator system including:
      a first indicator attached to the substrate in one or more first areas;
      a second indicator attached to the substrate in one or more second areas; and
      a reagent comprising urease attached to the substrate in the one or more second areas.
   wherein the first indicator is configured to change color when contacted by a vaginal secretion having a pH level associated with vaginosis or amniotic fluid leakage and the second indicator being configured to change color when contacted by urine reacting with the reagent, while not changing color when contacted by vaginal secretions having a pH level associated with vaginosis or amniotic fluid leakage.

9. The device of claim 8, wherein the substrate, first indicator and the second indicator are configured so that a color attained upon a color transition remains unchanged three hours after drying.

10. The absorbent body of claim 8, further comprising means for mounting the absorbent body in a position to absorb fluids secreted from a female's vaginal area.

11. The device of claim 10, wherein the first indicator and the second indicator each have a negatively charged functional group.

12. The absorbent body of claim 8, wherein the first indicator is configured to change color upon contact with amniotic fluid.

13. The absorbent body of claim 8, wherein the first indicator is configured to change color upon contact with vaginal secretions associated with vaginosis.

* * * * *

UNITED STATES PATENT AND TRADEMARK OFFICE
CERTIFICATE OF CORRECTION

PATENT NO.   : 6,627,394 B2
DATED        : September 30, 2003
INVENTOR(S)  : Kritzman et al.

It is certified that error appears in the above-identified patent and that said Letters Patent is hereby corrected as shown below:

Column 12,
Line 57, change "areas." to -- areas; --.

Column 14,
Line 2, change "areas." to -- areas; --.

Signed and Sealed this

Second Day of December, 2003

JAMES E. ROGAN
*Director of the United States Patent and Trademark Office*